United States Patent
Ward et al.

(10) Patent No.: US 10,271,740 B2
(45) Date of Patent: Apr. 30, 2019

(54) SYSTEM FOR PROVIDING CONTINUOUS SYSTOLIC BLOOD PRESSURE MEASUREMENT TO MAINTAIN PERMISSIVE HYPOTENSION

(71) Applicant: THE REGENTS OF THE UNIVERSITY OF MICHIGAN, Ann Arbor, MI (US)

(72) Inventors: Kevin R. Ward, Superior Township, MI (US); Hasan Alam, Ann Arbor, MI (US); Kayvan Najarian, Northville, MI (US); Robert Mitchell Baldwin, II, Grand Rapids, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 853 days.

(21) Appl. No.: 14/793,844

(22) Filed: Jul. 8, 2015

(65) Prior Publication Data
US 2016/0007863 A1 Jan. 14, 2016

Related U.S. Application Data

(60) Provisional application No. 62/021,957, filed on Jul. 8, 2014.

(51) Int. Cl.
*A61B 5/1455* (2006.01)
*A61B 5/0205* (2006.01)
(Continued)

(52) U.S. Cl.
CPC ............. *A61B 5/0205* (2013.01); *A61B 3/16* (2013.01); *A61B 5/022* (2013.01);
(Continued)

(58) Field of Classification Search
None
See application file for complete search history.

(56) References Cited

U.S. PATENT DOCUMENTS

2007/0060874 A1 3/2007 Nesbitt et al.
2007/0093701 A1 4/2007 Myers et al.
(Continued)

FOREIGN PATENT DOCUMENTS

WO WO-2014018024 A1 1/2014

OTHER PUBLICATIONS

International Search Report for International Application No. PCT/US2015/039476, dated Oct. 6, 2015.
(Continued)

*Primary Examiner* — Eric Winakur
*Assistant Examiner* — Marjan Fardanesh
(74) *Attorney, Agent, or Firm* — Marshall, Gerstein & Borun LLP

(57) ABSTRACT

A system for maintaining permissive hypotension in a patient includes monitoring of blood perfusion and pressure, combining blood perfusion and pressure data to determine systolic blood pressure, monitoring for detection of systolic blood pressure below a critical threshold value, and providing an alert to perfusion options to maintain permissive hypotension. The system may be adapted to adjust the critical threshold value for systolic blood pressure as treatment progresses.

9 Claims, 6 Drawing Sheets

(51) Int. Cl.
*A61M 16/00* (2006.01)
*A61B 3/16* (2006.01)
*A61B 5/022* (2006.01)
*A61B 5/053* (2006.01)
*A61F 7/00* (2006.01)
*A61M 5/172* (2006.01)
*A61B 5/02* (2006.01)
*A61B 5/0295* (2006.01)
*A61M 5/14* (2006.01)

(52) U.S. Cl.
CPC ........ *A61B 5/02028* (2013.01); *A61B 5/0295* (2013.01); *A61B 5/0531* (2013.01); *A61B 5/14552* (2013.01); *A61F 7/00* (2013.01); *A61M 5/1723* (2013.01); *A61M 16/0003* (2014.02); *A61B 5/14551* (2013.01); *A61F 2007/0093* (2013.01); *A61M 5/14* (2013.01); *A61M 2230/005* (2013.01); *A61M 2230/06* (2013.01); *A61M 2230/20* (2013.01); *A61M 2230/30* (2013.01)

(56) References Cited

U.S. PATENT DOCUMENTS

| | | |
|---|---|---|
| 2009/0018453 A1 | 1/2009 | Banet et al. |
| 2011/0028854 A1 | 2/2011 | Addison et al. |
| 2011/0066043 A1* | 3/2011 | Banet ............... A61B 5/022 600/485 |

OTHER PUBLICATIONS

Written Opinion of the International Searching Authority for International Application No. PCT/US2015/039476, dated Oct. 6, 2015.

* cited by examiner

SYSTEM FOR PROVIDING CONTINUOUS SYSTOLIC BLOOD PRESSURE MEASUREMENT TO MAINTAIN PERMISSIVE HYPOTENSION

CROSS-REFERENCE TO RELATED APPLICATIONS

This application claims the benefit of the filing date of U.S. Provisional Patent Application No. 62/021,957, filed Jul. 8, 2014. U.S. Provisional Patent Application No. 62/021,957 is hereby incorporated by reference.

FIELD OF THE DISCLOSURE

This disclosure relates generally to monitoring blood pressure of a mammal, such as a human, and more specifically, to a system for continuously monitoring systolic blood pressure of a mammal, e.g. a human, in a non-invasive manner, and utilizing collected data to advise a clinician on measures necessary to safely maintain permissive hypotension.

BACKGROUND

Bleeding (hemorrhage) causes 30-50% of all trauma-associated deaths. Permissive hypotension or hypotensive resuscitation in pre-hospital and critical care environments helps prevent re-bleeding from severe injuries. Restoration of blood pressure after trauma or uncontrolled hemorrhage can actually be detrimental by causing more bleeding. Maintenance of low but critical level of systolic blood pressure can reduce bleeding and help preserve a minimal level of tissue perfusion. A minimum level of systolic blood pressure (70-90 mmHg) is needed to maintain a critical level of coronary and cerebral perfusion pressure to prevent cardiovascular or cerebral collapse. When brain injury is present, minimum values may need to be higher. In order to safely practice permissive hypotension, continuous non-invasive blood pressure monitoring is essential in maintaining permissive hypotension, but is challenging in the pre-hospital setting. Invasive blood pressure monitoring while allowing for continuous monitoring is not practical. It is also associated with risk such as infection. Even in the hospital setting, invasive monitoring is not always practical.

Photoplethsmography (PPG) (pulse oximetry) provides a noninvasive measure of arterial hemoglobin oxygen saturation. The technology relies on pulsatile flow to the finger or other part of an extremity. Very little pulsatile flow is required to produce this reading. Other technologies such as passive piezoelectric sensors are capable of picking up pulsatile flow as well but as opposed to the PPG which senses flow, piezoelectric sensors measure the mechanical expansion and contraction of the arterial vessel wall in response to pulsatile flow. Applanation tonometry, Doppler signal, bioimpedence sensor, or light spectroscopy are suitable alternatives for pulsatile or piezoelectric sensors. This invention uses a cuff or other pressure-producing device to make a measurement necessary to provide health care provider scheduled knowledge of both the current systolic pressure as well as when systolic blood pressure has been reduced to a critical threshold. The invention can be used in conjunction with other devices to create a closed loop feedback system to maintain critical blood pressure and other perfusion values. The PPG, piezoelectric sensors, applanation tonometry, Doppler signal, or light spectroscopy sensors may be disposed either distal to the cuff or other pressure producing component, under the pressure producing component, or both distal and under the pressure producing component.

It is well known that the use of an inflatable blood pressure cuff when coupled with a distal PPG can be used to determine systolic blood pressure. Systolic blood pressure can be determined by inflating the blood pressure cuff to a level that causes the disappearance of the PPG signal. However, continuous measurement of systolic blood pressure by this manner is not advised as ischemia would result. Furthermore it is not necessary to do this to practice permissive hypotension. Current automated oscilliometic non-invasive blood pressure devices are ill suited to dynamically monitor blood pressure for permissive hypotension.

SUMMARY

The system of the present disclosure combines a non-invasive blood perfusion measurement and a cuff or other pressure producing device to automatically intermittently determine current systolic blood pressure as well as determine when blood pressure has been reduced below a critical value. The system alerts clinicians to changes in blood pressure and also advises the clinician as to appropriate perfusion options. This system would thus help clinicians maintain permissive hypotension more effectively and help reduce deaths from severe trauma.

According to the present disclosure, a mechanical system combined with a computation system is provided that allows patient-specific targeting of a specific permissive hypotension blood pressure. This targeted blood pressure, since it would reside below normal systolic blood pressure, would not produce ischemia distal to the inflating blood pressure cuff or other pressure-producing device. As an example, the user (e.g., a medical clinician or paramedic) may apply the system to an injury victim and set the system to continuously monitor for a reduction below a minimum systolic blood pressure by inflating the cuff or other pressure-producing device to the minimum systolic blood pressure (e.g. 80 mmHg). If the victim's actual systolic blood pressure is above this targeted minimum systolic blood pressure value, the PPG or PZT or other flow or vascular signal will be active. A loss of signal is indicative of a drop below the minimum pressure (systolic has dropped below the cuff or other pressure-producing device). This would indicate the need for treatment to raise the pressure. During this time, the device automatically will change cuff or pressure to find the new current systolic blood pressure. Once found, and treatment begins, the algorithm will change the pressure in the cuff to seek the new systolic blood pressure. Once above the minimum, the device will intermittently find the true systolic blood pressure and then decrease to the minimum cuff or constrictive band pressure (e.g. 80 mmHg). In order to reduce reperfusion injury of the limb distal to the cuff or constrictive band, the device, via its algorithms, will totally deflate for various periods of time at various intervals followed by reactivation to find actual systolic blood pressure and then monitor for systolic blood pressures below a minimal threshold.

When coupled with other sensors, a system can be created that through machine learning and other artificial intelligence techniques can be used in a closed loop fashion to optimize blood pressure and tissue perfusion.

DETAILED DESCRIPTION OF THE PREFERRED EMBODIMENTS

Figure 1:
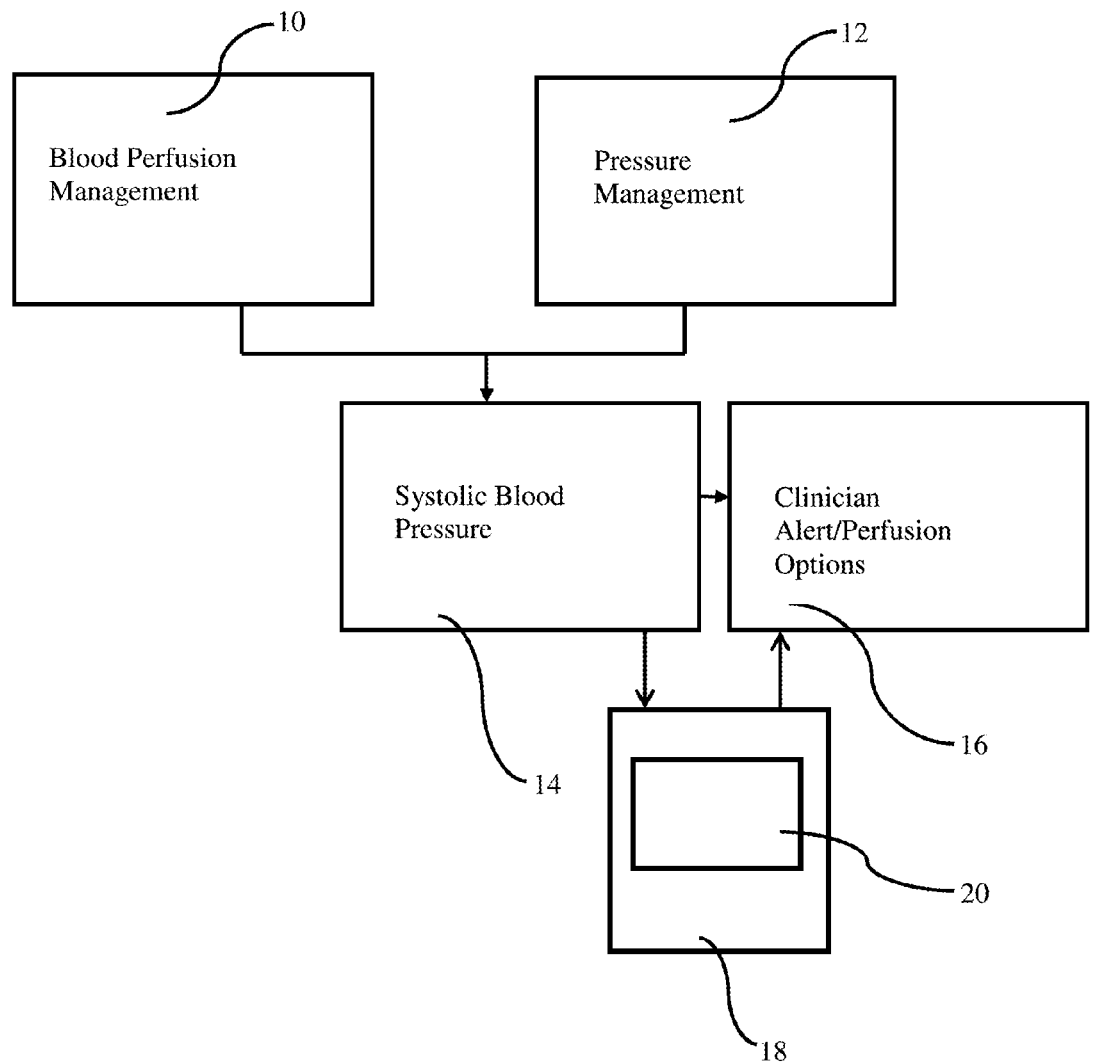
FIG. 1 is a schematic diagram of a system of the present disclosure for monitoring systolic blood pressure of a mammal, e.g. a human, and alerting a clinician as to perfusion options based on the measured systolic blood pressure.

With reference to FIG. 1, a non-invasive blood perfusion measuring means 10 and a cuff-based pressure measuring means 12 are taken of a mammal, e.g., a human, from which a systolic blood pressure measurement 14 can be determined. Based on that systolic blood pressure measurement 14, the system is provided with means to alert a clinician as to perfusion options that permit the maintenance of permissive hypotension.

The system includes a processor 18 in communication with a memory 20. The memory 20 stores information concerning ideal systolic blood pressure for maintaining permissive hypotension based on one or more parameters, such as a patient's age, gender, weight, or injury type. The processor 18 is programmed to compare the systolic blood pressure (determined based on the blood perfusion data collected by the blood perfusion measuring means 10 and the pressure data collected by the pressure measuring means 12) to data stored in the memory 20 and send an alert, such as to a display 16, recommending a clinician as to perfusion options that permit the maintenance of permissive hypotension.

In an exemplary embodiment, a blood perfusion measuring device 10, such as a PPG or PZT sensor, and a cuff-based pressure device 12 are applied to a patient's extremity. More specifically, as used herein, it is to be appreciated that references to a cuff-based pressure device 12 include a cuff, which provides a source of constrictive pressure in order to restrict blood flow to tissue distal to where the cuff is applied, and a pressure sensor (e.g., a pressure transducer). For instance, a blood pressure cuff 12 is secured around the patient's upper arm and the blood perfusion device is attached to the finger. Based on data obtained by the blood perfusion measuring device 10 and the cuff-based pressure device 12, the systolic blood pressure of the patient is continuously monitored. A controller or processor 18 is provided in communication with the blood perfusion measuring device and the cuff-based pressure measuring device. The processor 18 is provided with a memory that stores a predetermined value corresponding to a minimum systolic blood pressure threshold. For instance, this threshold may be 80 mmHg. So long as the measured actual systolic blood pressure is above this threshold, the PPG or PZT signal of the system of the present disclosure remains active. In the event the patient's systolic blood pressure drops below the threshold (which may be indicated by a loss of signal from the blood perfusion measuring device and the cuff-based pressure measuring device), indicating a need for treatment to increase pressure, the processor 18 directs the cuff-based pressure device 12 to adjust in tightness so as to find a new current systolic blood pressure. In all of these instances, pressure is sensed in the cuff via a pressure transducer and systolic pressure is determined by matching it with the loss of the PPG, PZT, or other flow or vascular signal. Alternatively, a pressure sensor could be placed between a pressure based cuff or other pressure producing device and the surface of the patient's skin to measure applied pressure.

Upon detection of the new current systolic blood pressure, and treatment begins to increase the patient's blood pressure, an algorithm programmed into the logic of the processor 18 detects this change in state and the controller signals the cuff or constrictive band to seek the new systolic blood pressure. When the systolic blood pressure is again above the minimum threshold, the true systolic blood pressure is at least intermittently detected and the processor 18 signals the cuff or constrictive band to decrease in pressure until systolic pressure is sustained at or just above the threshold systolic pressure.

Figure 2:
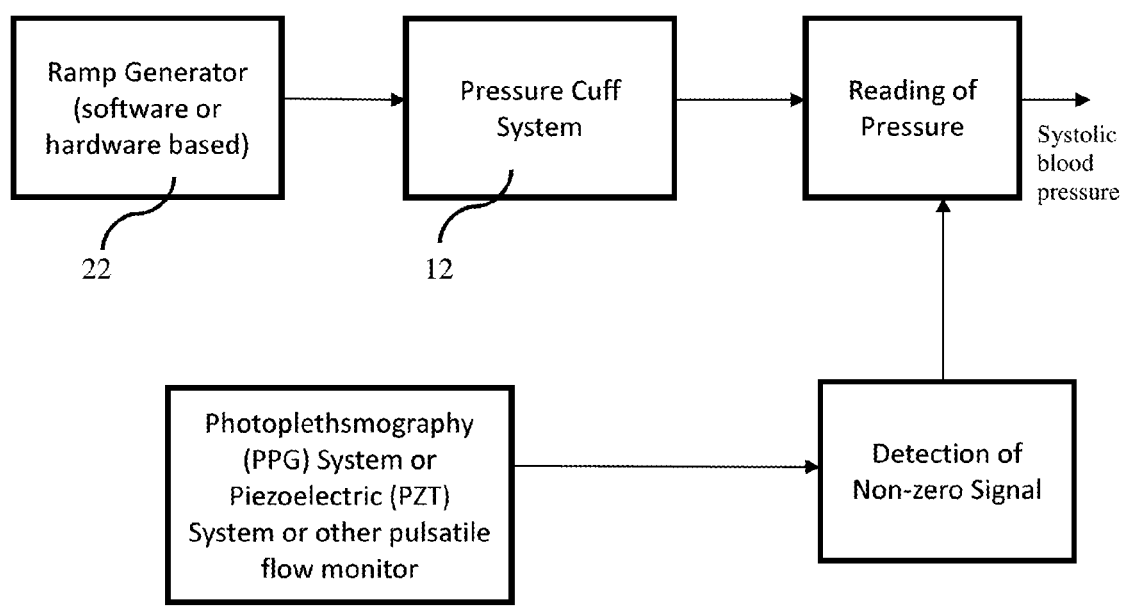
FIG. 2 is a schematic illustration of an exemplary implementation of the system of the present disclosure.

It is recognized that constant application of constrictive force to the limb of an injured patient can result in ischemia. To alleviate this risk, the system of the present disclosure is preferably configured to permit the pressure cuff or other pressure-producing device of the cuff-based pressure device 12 to completely deflate for various periods of time, at various intervals, and subsequently re-inflate to find actual systolic blood pressure and monitor for systolic blood pressure dropping below the minimum threshold. The periods of time and intervals of such deflation and re-activation can be regular or irregular, and can be constant or varying. A ramp generator 22 (see FIG. 2) may be employed to control the cuff-based pressure measuring device 12.

Figure 3:
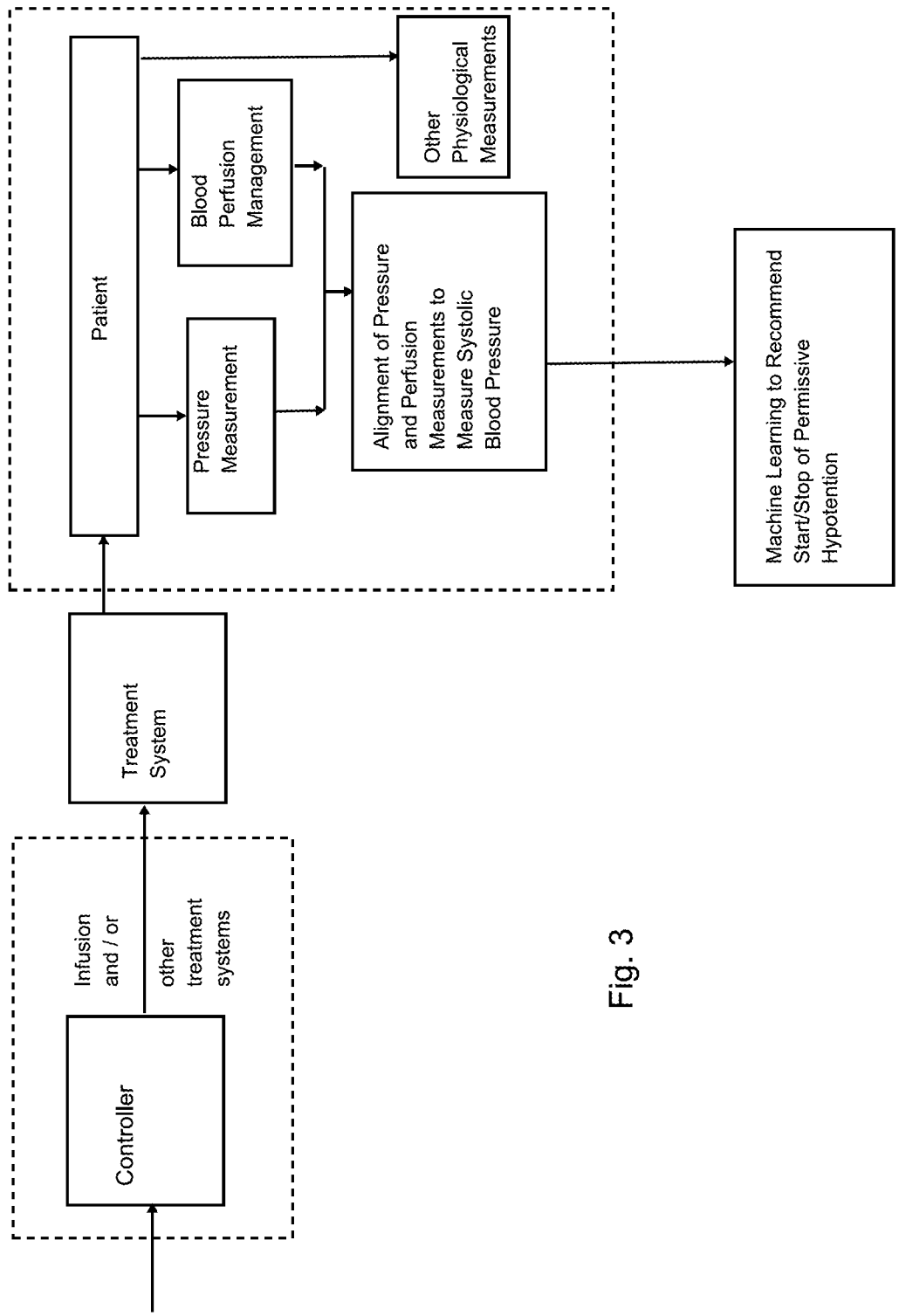
FIG. 3 is a schematic illustration of the system of the present disclosure, used in conjunction with other physiologic sensors.
Figure 4:
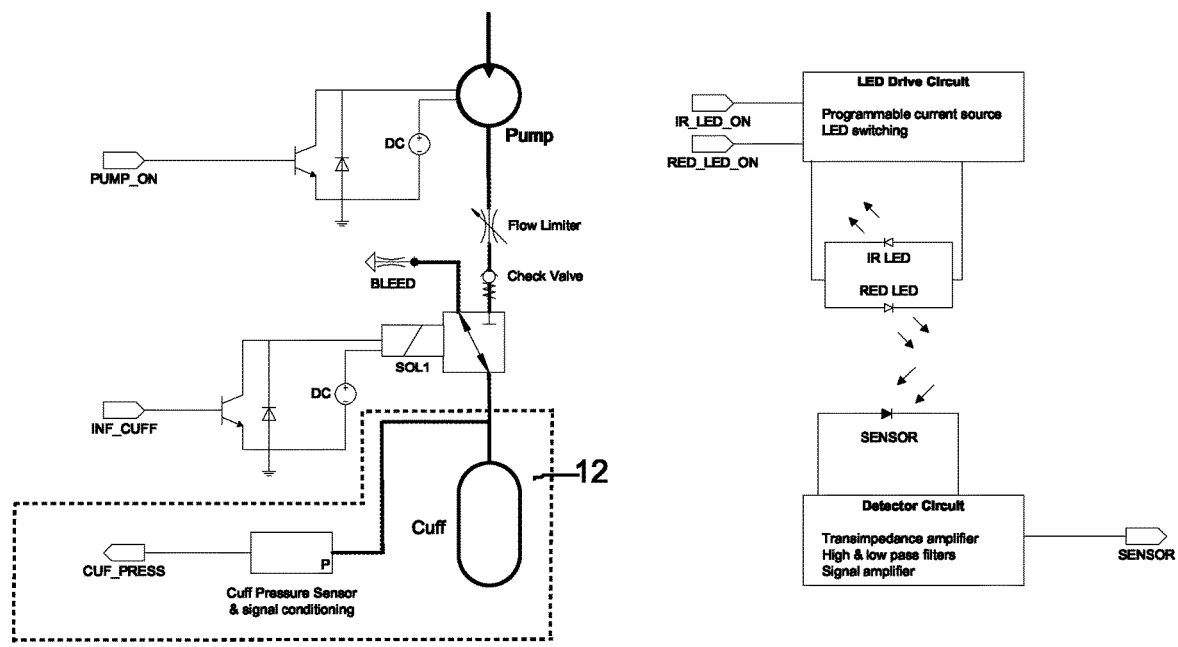
FIG. 4 is a schematic diagram of one embodiment of the present invention showing its functional subsystems and connections between subsystems.
Figure 4:
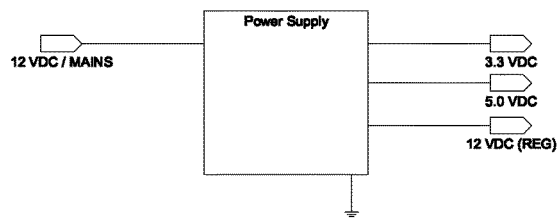

As illustrated in FIG. 3, through the use of machine learning or artificial intelligence techniques, the system of the present disclosure is suitable for use in a closed-loop fashion, in conjunction with other sensors, to optimize blood pressure and tissue perfusion. For example, if the piezoelectric (PZT) sensor is used distal to the inflating cuff or other pressure producing device, in addition to detecting systolic blood pressure, a measure of vascular reactivity can be obtained. Other tissue perfusion measures including those distal or proximal to the inflating cuff or other pressure-producing device can also be used to detect the state of perfusion and provide information to the system to optimized the balance between blood pressure and tissue perfusion. Examples of these could be tissue oxygenation monitors such as near infrared, visible light or Raman spectroscopy, and other flow perfusion measures such as laser Doppler or speckle tracking devices, or volumetric measures such as impedance cardiac output, ultrasound, and others. This is envisioned to assist in balancing the needs of a critical perfusion pressure with that of vital blood and oxygen perfusion.

While the primary purpose of the invention is to assist in the management of the critically injured patient who may be bleeding, the described invention could also be used to help guide treatment of those in cardiovascular collapse form other causes such as cardiac arrest. In this setting during cardiopulmonary resuscitation it would be advantageous in knowing the systolic pressure produced during chest compressions to ensure a minimum systolic pressure and tissue perfusion. The systems could be used to guide and provide closed loop feedback to treatment devices such as mechanical chest compressors and infusion pumps in a manner described for its use in the hemorrhaging subject.

In an alternative embodiment a means for acquiring the patient's electrocardiogram (ECG) signal is added to the system, such as placing a plurality of leads at strategic anatomical positions on a patient, each of which measures voltage, and based on those measurements, plotting cardiac biopotential activity. Analysis of the ECG waveform by software identifies the P and/or R waves, which generally corresponds with contraction of the ventricles of the heart and thus the pressure wave that ultimately results in the pulse pressure and flow sensed peripherally. Since the magnitude of this systolic pressure wave is the primary determinant of the resultant blood flow rate, the time elapsed from the P and/or R waves to sensing the pulse peripherally, called the pulse transit time (PTT), has been shown to correlate with systolic pressure.

One shortcoming of using PTT as a technique for indicating systolic blood pressure is its dependence on the vascular resistance of the individual patient. This shortcoming is overcome in the present invention through the use of blood pressure measurements made with the cuff and PPG technique described above as a means of calibrating the PTT measurements for the individual patient. In this embodiment, PTT is monitored any time a peripheral PPG signal is available, and the scale used to correlate the PTT measurement to systolic blood pressure is recalibrated any time the cuff and PPG sensor combination successfully determines systolic blood pressure. This correlation is then used to provide a virtually continuous systolic pressure reading whenever systolic blood pressure is maintained at or above the cuff pressure, which represents a majority of the treatment time. This virtually-continuous measurement of systolic blood pressure may then be used to alert the care giver of substantial increases in systolic blood pressure. The device may then direct therapeutic options for lowering systolic blood pressure back toward the desired threshold. An additional PPG or PZT signal can be used in place of the ECG signal for PTT monitoring.

An additional unique feature of the current invention is the ability to incorporate sensors under the cuff pressure producing device which may include incorporating the sensors into the cuff itself. As an exemplary example, a PPG, PZT, or other flow or vascular sensor could be attached to the inner surface of the pressure producing device making contact with the skin surface. As the pressure producing device is activated and reaches a pressure exceeding systolic blood pressure, the signal is lost. This iteration of the device can also be coupled with sensors distal to the cuff pressure producing device as a means to ensure the robustness of the measure of systolic blood pressure.

Figure 5:
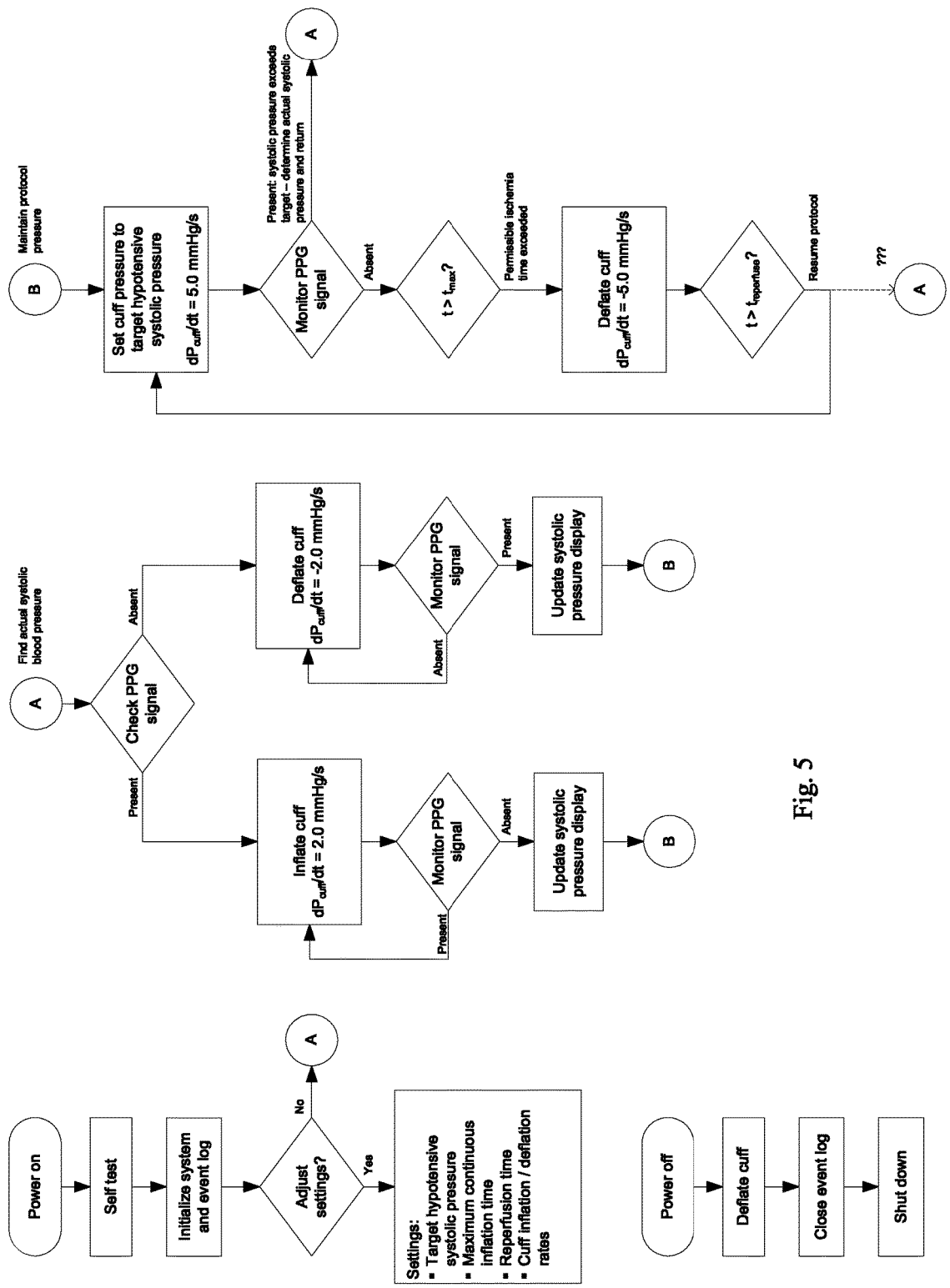
FIG. 5 is a flow chart diagramming the software logic flow of one embodiment of the present invention.

Turning to FIG. 5, a flow chart diagramming the software logic flow of one embodiment of the present invention is illustrated, which logic can be written into a software program that is stored on a non-transitory computer readable medium. From left to right, upon power-on, after an initializing self-test and system and event log initialization, a decision box is set to adjust settings, including a target hypotensive systolic pressure, maximum continuous cuff inflation time, reperfusion time, and cuff inflation/deflation rates. When there is a decision not to change settings, the software carries out a series of commands that performs the logic diagrammed in the logic tree headed by the circle "A". Namely, the system is checked for a PPG signal.

If the PPG signal is present, the controller is signaled to initiate inflation of the cuff at a rate of 2.0 mmHg/s. The PPG signal is continually monitored, and so long as present, inflation of the cuff continues. Once the PPG signal is absent, a systolic pressure display is updated with the patient's systolic pressure, and the software carries out a series of commands that performs the logic diagrammed in the logic tree headed by the circle "B".

If the PPG signal is absent upon initial checking for the PPG signal, the controller is signaled to deflate the cuff at a rate of −2.0 mmHg/s. The PPG signal is continually monitored, and so long as absent, deflation of the cuff continues. Once the PPG signal is present, the systolic pressure display is updated with the patient's systolic pressure, and the software carries out the series of commands that performs the logic diagrammed in the logic tree headed by the circle "B".

According to the logic sequence headed by the circle "B", protocol pressure is maintained. The cuff pressure is set to achieve and maintain a target hypotensive systolic pressure, such as at a rate of 5.0 mmHg/s. The system is checked for a PPG signal. If present, this condition is indicative of systolic pressure exceeding a target value. The system in that circumstance needs to determine the actual systolic pressure, so the software again carries out the series of commands that performs the logic diagrammed in the logic tree headed by the circle "A". If the PPG signal is absent, the system checks to see whether a time threshold, $t_{max}$, which corresponds to a permissible ischemia time, has been exceeded. Once this time threshold is exceeded, the controller is signaled to deflate the cuff at a rate of 5.0 mmHg/s. The system can then monitor a period of time during which the cuff is deflating until a threshold time corresponding to a time after which reperfusion should occur, and upon detecting sufficient time has elapsed, the system resumes protocol by again inflating the cuff at a rate of 5.0 mmHg/s.

When the system is powered off, the controller is signaled to deflate the cuff, the event log is closed, and the system shuts down.

Figure 6:
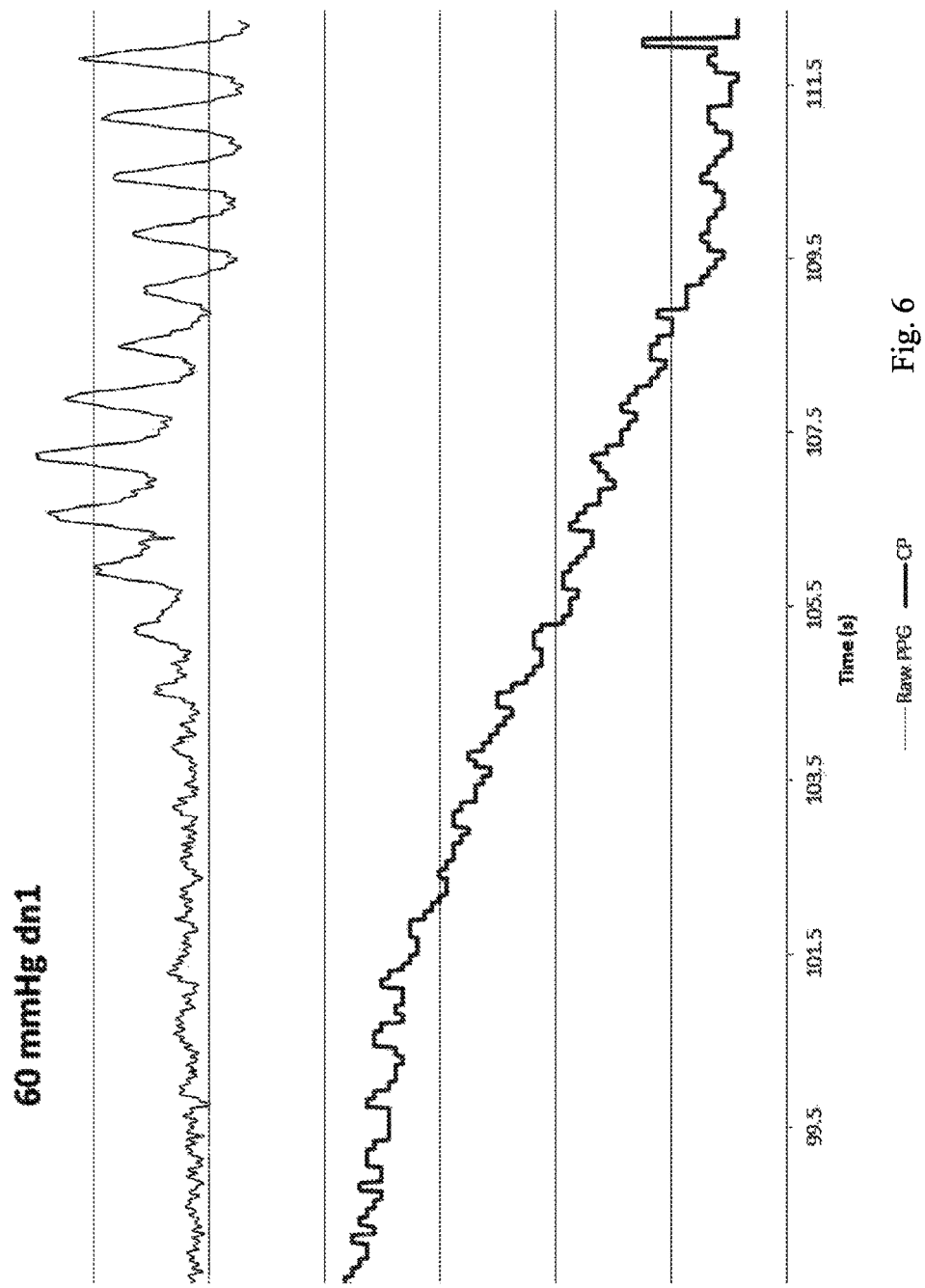
FIG. 6 is a plot of the PPG and intra-cuff pressure as the cuff pressure is reduced below the systolic blood pressure and in particular how the pulsatile nature of the PPG signal returns once the cuff pressure falls below the systolic blood pressure.

FIG. 6 is a plot of the PPG and intra-cuff pressure as the cuff pressure is reduced below the systolic blood pressure. The plot diagrams how the pulsatile nature of the PPG signal returns once the cuff pressure falls below the systolic blood pressure.

While various embodiments of the invention are described herein, it will be appreciated that variations may be made that are still within the scope of the appended claims.

What is claimed is:

1. A system for monitoring systolic blood pressure of a patient, comprising:
    a blood perfusion monitoring means;
    a pressure monitoring means;
    a controller, the controller configured for combining blood perfusion data collected by the blood perfusion monitoring means and pressure data collected by the pressure monitoring means to determine systolic blood pressure, the controller further comparing the collected data to data stored in memory; and
    an alerting means, activated by the controller, for alerting a caregiver as to perfusion options to maintain permissive hypotension in the patient, the activation by the controller based on the intermittent determination of current systolic blood pressure by the controller and by monitoring by the controller for detection of systolic blood pressure below a critical threshold value; wherein the controller is further configured for directing adjustment of the pressure monitoring means when the controller determines that systolic blood pressure is below the critical threshold.

2. The system of claim 1, the controller configured for finding current systolic blood pressure in addition to monitoring for a reduction in systolic blood pressure below a critical threshold followed by finding the new current systolic blood pressure as treatment ensues.

3. The system of claim 1, where the pressure monitoring means consists of a mechanically inflating cuff or mechanically induced pressure band configured to extend around any part of an extremity and capable of producing small incremental step wise increases or decreases in pressure around any part of an extremity.

4. The system of claim 3 where the blood perfusion monitoring means used in conjunction with the pressure monitoring means is selected from the group consisting of a pulse plethysmography sensor, a piezoelectric sensor, applanation tonometry, Doppler signal, light spectroscopy, a bioimpedence sensor, or other sensor capable of detecting a loss of pulsatile flow either distal to the pressure monitoring means, under the pressure monitoring means, or both distal and under the pressure monitoring means.

5. The system of claim 1, wherein the controller is configured for determining the systolic blood pressure based upon parameters of tissue perfusion and vascular reactivity collected by at least one of a piezoelectric sensor, a tissue oxygenation monitor, a laser tracking device, a Doppler tracking device, a speckle tracking device, an impedance cardiac output device, and an ultrasound device.

6. The system of claim 1, wherein the controller is configured for determining pulse transit time by coupling pressure data collected by the pressure monitoring means with at least one of ECG, PPG, piezoelectric (PZT), bioimpedence, or other perfusion or vascular signals that are obtained proximal to the pressure monitoring means by at least one of the blood perfusion monitoring means, a means for acquiring an electrocardiogram, a piezoelectric sensor, a tissue oxygenation monitor, a laser tracking device, a Doppler tracking device, a speckle tracking device, an impedance cardiac output device, and an ultrasound device.

7. The system of claim 1 where the determined systolic blood pressure is then provided, by the controller, to treatment devices that are used to make therapy recommendations or drive therapies to maintain targeted levels of blood pressure and tissue perfusion in a closed loop or semi-closed loop fashion using one or more additional devices.

8. The system of claim 7, wherein the one or more additional devices includes an infusion pump, a hemostatic device, or a ventilator.

9. The system of claim 1, wherein the memory stores and the controller is configured to use at least one of injury type, pattern, gender, race, and estimated transport time to determine optimal minimum perfusion pressure.

* * * * *